United States Patent [19]

Katsuragi et al.

[11] Patent Number: 4,817,620

[45] Date of Patent: Apr. 4, 1989

[54] NONCONTACT TYPE TONOMETER

[75] Inventors: Kenjiro Katsuragi; Katsuhiko Kobayashi; Yoshitaka Torii, all of Tokyo, Japan

[73] Assignee: Tokyo Kogaku Kikai Kabushiki Kaisha, Tokyo, Japan

[21] Appl. No.: 92,536

[22] Filed: Sep. 3, 1987

[30] Foreign Application Priority Data

Sep. 6, 1986 [JP] Japan ................... 61-209945

[51] Int. Cl.⁴ ............................................. A61B 3/16
[52] U.S. Cl. ..................... 128/648; 128/652
[58] Field of Search ............... 128/648, 645, 748, 649, 128/650, 651, 652

[56] References Cited

U.S. PATENT DOCUMENTS

| | | | |
|---|---|---|---|
| 3,232,099 | 2/1966 | Motchenbacher | 128/648 |
| 3,756,073 | 9/1973 | Lavallee et al. | 128/648 |
| 4,665,923 | 5/1987 | Kobayashi | 128/648 |
| 4,705,045 | 11/1987 | Nishimura | 128/648 |

FOREIGN PATENT DOCUMENTS 183621 6/1986 European Pat. Off. ............ 128/648

Primary Examiner—Edward M. Coven
Attorney, Agent, or Firm—Finnegan, Henderson, Farabow, Garrett & Dunner

[57] ABSTRACT

A non-contact type tonometer is disclosed. It includes a fluid discharging device for discharging a fluid from a nozzle towards an eye to be tested and transfiguring the eye, an eye pressure measuring device for measuring the eye pressure of the eye based on the pressure of the fluid, and an alignment detecting device for detecting the aligning state of the nozzle of the fluid discharging device. It further includes an eye pressure value correcting device for correcting an actually measured eye pressure value obtained by the eye pressure measuring device based on an alignment error information of the nozzle with respect to the eye using the alignment detecting device.

9 Claims, 7 Drawing Sheets

F I G. 4
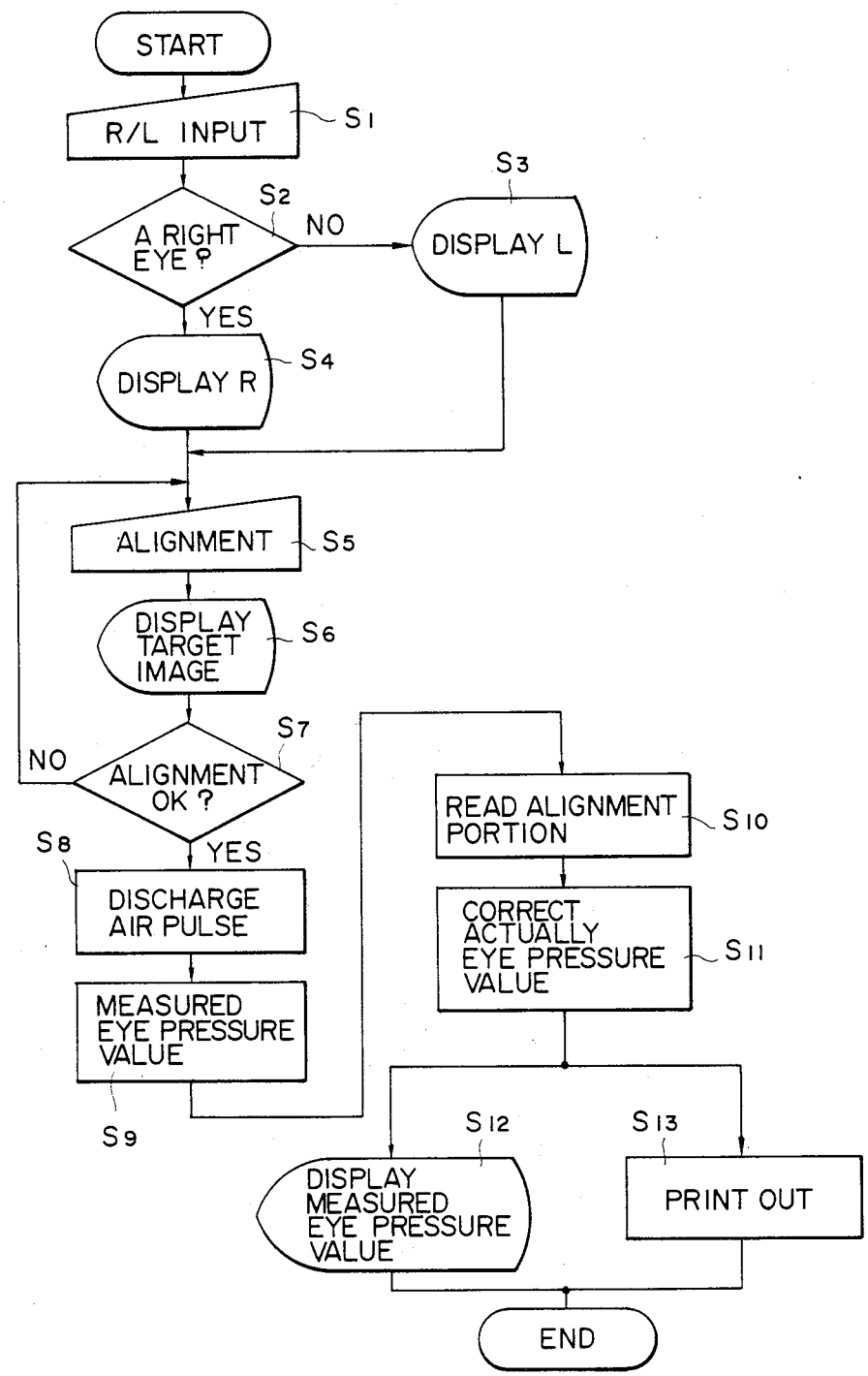

NONCONTACT TYPE TONOMETER

BACKGROUND OF THE INVENTION

1. Field of the Invention

This invention relates to a noncontact type tonometer for discharging a fluid from a nozzle towards an eye to be tested to transfigure the eye and measuring the eye pressure thereof based on a fluid pressure when the eye has been transfigured by a predetermined amount.

2. Prior Art of the Invention

Heretofore, there has been known a noncontact type tonometer, in which a fluid such as an air pulse is discharged toward the cornea of an eye to be tested and the pressure of the eye is measured based on the pressure of the air pulse when the eye has been transfigured by a predetermined amount. However, this noncontact type tonometer has the shortcoming in that unless the vertical, rightward and leftward, and forward and backward alignments are accurate between the nozzle of a fluid discharging means for discharging an air pulse towards the eye and the vertex of the cornea of the eye, an error is occurred to an eye pressure value obtained by an eye pressure measuring means. In view of the foregoing, the conventional noncontact type tonometer is provided with an alignment detecting means for detecting the accurate alignment of the nozzle with respect to the eye to be tested.

If the nozzle of the fluid discharging means can be accurately aligned with respect to the eye using the alignment detecting means, an accurate eye pressure value can be obtained. However, since the eye to be tested is often accompanied with the problem of a minor fluctuation of the fixation of sight, the accurate alignment is difficult to obtain. Moreover, it takes much time to verify the alignment of the nozzle with respect to the eye to be tested. In addition, there is such a problem as that unless a person who has a long experience in such alignment verification, the accurateness of the alignment verification cannot be assured.

SUMMARY OF THE INVENTION

It is therefore a first object of the present invention to provide a noncontact type tonometer, which includes an eye pressure value correcting means for correcting an actually measured eye pressure value by an eye pressure measuring means based on an alignment error information of a nozzle with respect to an eye to be tested using an alignment detecting means, and in which even if an alignment verification of the nozzle is not accurately performed with respect to the eye using the alignment detecting means, a normal eye pressure in a normally aligned state can be obtained from an actually measured eye pressure value including an alignment error, based on an alignment error information as a displaced-amount from the normally aligned state.

A second object of the present invention is to provide a noncontact type tonometer which is convenient to carry by hand.

According to the present invention, it is possible to provide a tonometer, in which even if the alignment between the nozzle of the fluid discharging means and the eye to be tested is somewhat rough, the actually measured eye pressure value obtained in the rough alignment state can be corrected based on the alignment error amount, and thereby a normal eye pressure value can be obtained.

BRIEF DESCRIPTION OF THE DRAWINGS

FIG. 4 is a flow chart showing a measuring means;

PRINCIPLE OF THE INVENTION

Before describing the embodiment of the present invention, the principle of the present invention will be described with reference to FIG. 7.

Figure 7:
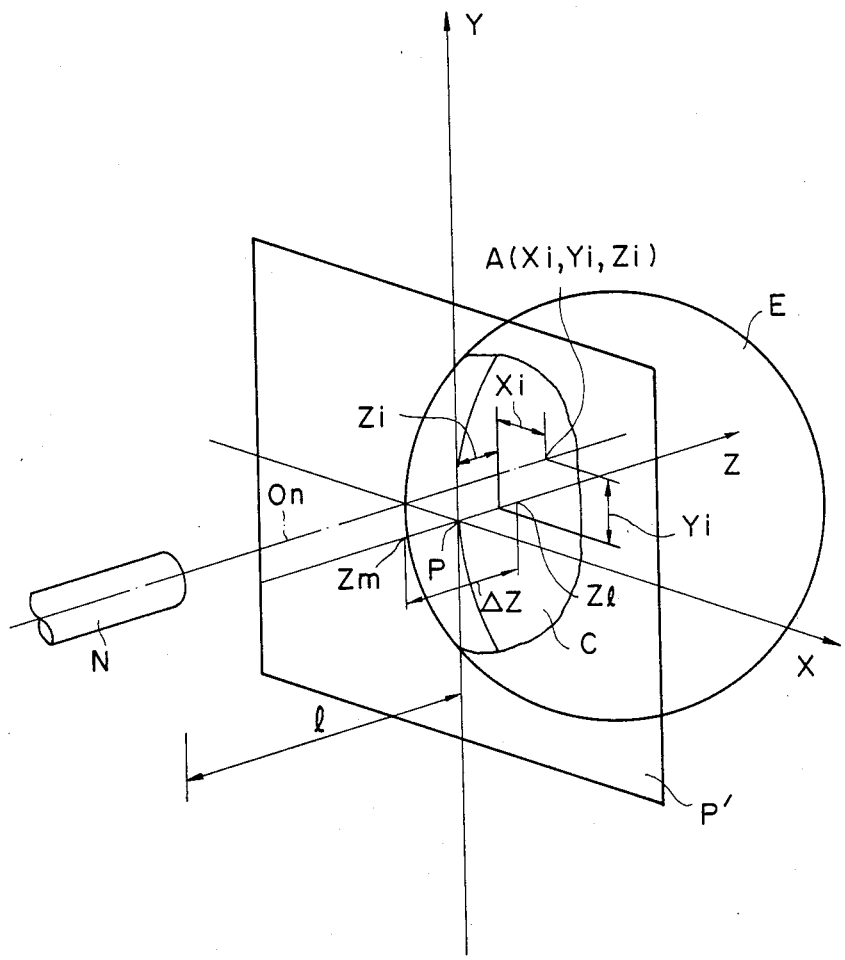
FIG. 7 is a schematic view for explaining the principle of the non-contact type tonometer according to one embodiment of the present invention.

In FIG. 7, symbolic reference character E denotes an eye to be tested, and P denotes the vertex of the cornea of the eye. P' denotes a contacting plane including the corneal vertex P. Z denotes an axis normal to the contacting plane P'. X and Y denote axes intersecting the axis Z at the corneal vertex P within the contacting plane P'. The corneal vertex P is served as the origin. The expression "normally aligned state" as used herein means that the tip of a nozzle N is positioned as such that the axis $O_n$ of the nozzle N of a fluid discharging means is in alignment with the Z axis, and a distance l between the tip of the nozzle N and the corneal vertex P becomes a normal working distance. An eye pressure of an eye E to be tested, which is measured in the normally aligned state, is defined as a "normal eye pressure $P_o$". On the contrary, when the tip of the nozzle N is displaced from its normally aligned position in the X, Y, and Z directions by $A(X_i, Y_i,$ and $Z_i)$, this state is expressed as that an "alignment error is present" with respect to the normally aligned state, and $A(X_i, Y_i,$ and $Z_i)$ represents an alignment error amount or an alignment position. A pressure of the eye E, which is measured in the state where the alignment error is present, is defined as an alignment error eye pressure $_iP''$.

At that time, the following functional equation can be obtained between the alignment error eye pressure $_iP$ and the normal eye pressure $P_o$;

$$P_o = f(_iP, X_i, Y_i, \text{ and } Z_i) \ldots \quad (1)$$

This equation means that if the alignment error eye pressure $_iP$ as an actually measured value and the alignment error amount $A(X_i, Y_i,$ and $Z_i)$ can be known, the normal eye pressure $P_o$ can be obtained.

The present invention is based on the above-mentioned principle. In order to obtain the normal eye pressure $P_o$, this functional equation is theoretically or experimentally sought, this functional equation is prepared in advance, an alignment error amount $A(X_i, Y_i,$ and $Z_i)$ is obtained when a certain actually measured eye pressure value came to be available, and both of these informations $A(X_i, Y_i,$ and $Z_i)$ and $_iP$ are substituted for the equation (1). Without seeking for the functional equation, the normal eye pressure $P_o$ can be obtained as follows. Namely, an alignment error amount $A(X_i, Y_i,$ and $Z_i)$ is given to the eye of a known normal eye pressure value $P_o$, the alignment error eye pressure $_iP$ is experimentally sought when the alignment error amount $A(X_i, Y_i, \text{ and } Z_i)$ is given, a correlation among the alignment error eye pressure $_iP$ as an actually measured value, the alignment error amount $(X_i, Y_i, \text{ and } Z_i)$ and the normal eye pressure $P_o$, is sought as a correlation table, the alignment error amount $A(X_i, Y_i \text{and } Z_i)$ is obtained when a certain actually measured eye pressure value $_iP$ came to be available, and the normal eye pressure $P_o$ is sought based on the correlation table. Such obtained normal eye pressure value $P_o$ is hereinafter referred to as a "corrected eye pressure value $P_o$" because it has been obtained by correction.

DETAILED DESCRIPTION OF THE EMBODIMENT

Figure 1:
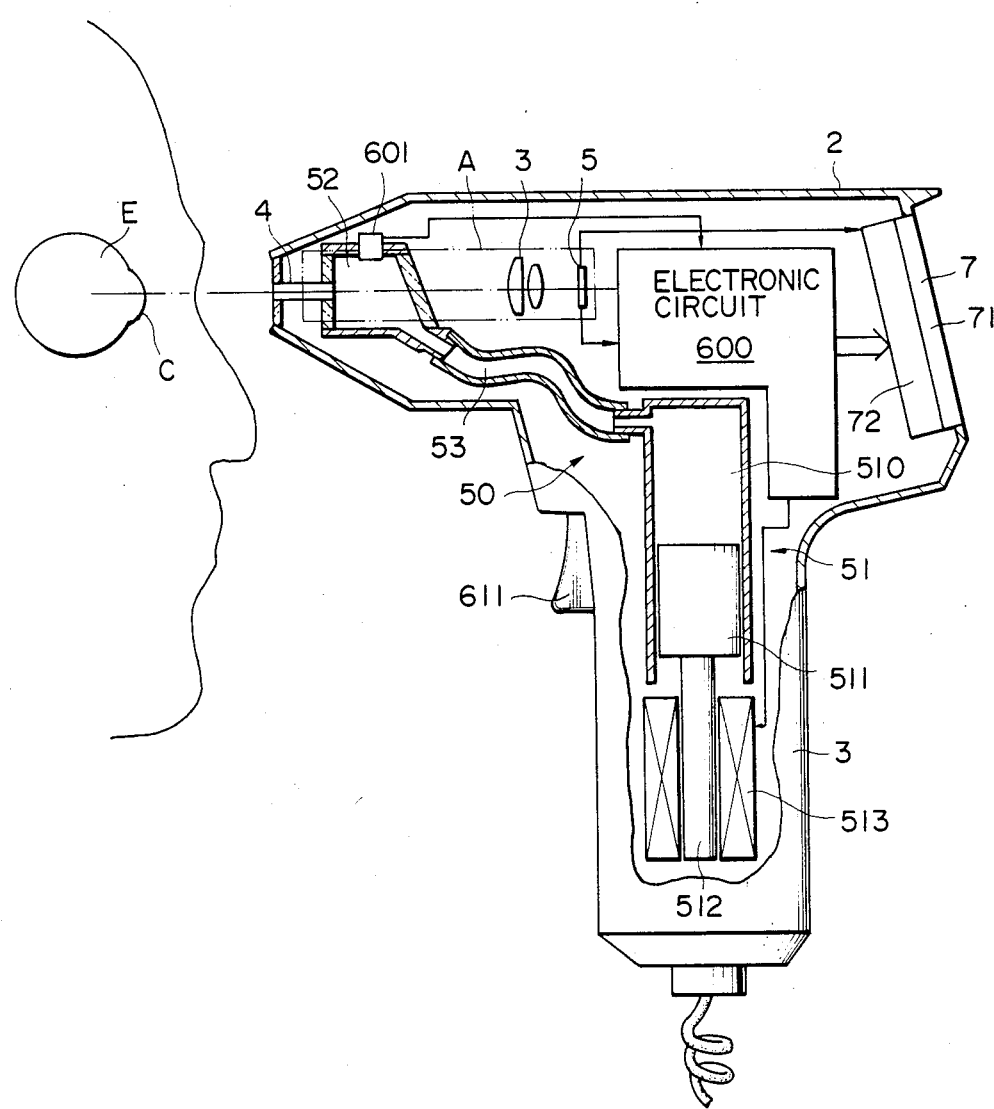
FIG. 1 is a schematic view showing a main body of a noncontact type tonometer according to one embodiment of the present invention.

FIG. 1 is an illustration, in which the present invention is incorporated in a portable or hand-held type tonometer. This tonometer is of the type that an eye pressure is measured by approaching the tonometer towards the eye E to be tested holding a holder 3 thereof by hand. A casing 2 is provided with an alignment detecting means A, a fluid discharging means 50 for discharging an air pulse as a fluid, an electronic circuit 600 having such a function as to generate an alignment displaying signal, to measure an eye pressure and the like, and a displaying means 7 for displaying an image of the anterior portion of the eye, the aligned state and the eye pressure value, all contained therein.

The fluid discharging means 50 comprises an air intaking/compressing portion 51, an air chamber 52 having a nozzle 4, and a flexible tubular body 53 for connecting the air intaking/compressing portion 51 and the air chamber 52 with each other. The air intaking/compressing portion 50 is contained within the holder 3. The air intaking/compressing portion 51 has a cylinder 510. The cylinder 510 is provided with a piston 511 vertically movably fitted therein. The piston 511 is mounted on the front end of a piston rod 512 made of a permanent magnet. The piston rod 512 is inserted into an electromagnetic solenoid 513. When the electromagnetic solenoid 513 has been excited, the piston rod 512 is caused to move upwards, the piston 511 is caused to compress air within the cylinder 510, the compressed air is caused to flow within the air chamber 52 through the tubular body 53, and the compressed air within the air chamber 52 is projected to the cornea C of the eye E as an air pulse from the nozzle 4. The air chamber 52 is provided with a pressure sensor 601 for detecting the pressure of the compressed air within the air chamber 52. Reference numeral 611 denotes a measuring switch.

Figure 2:
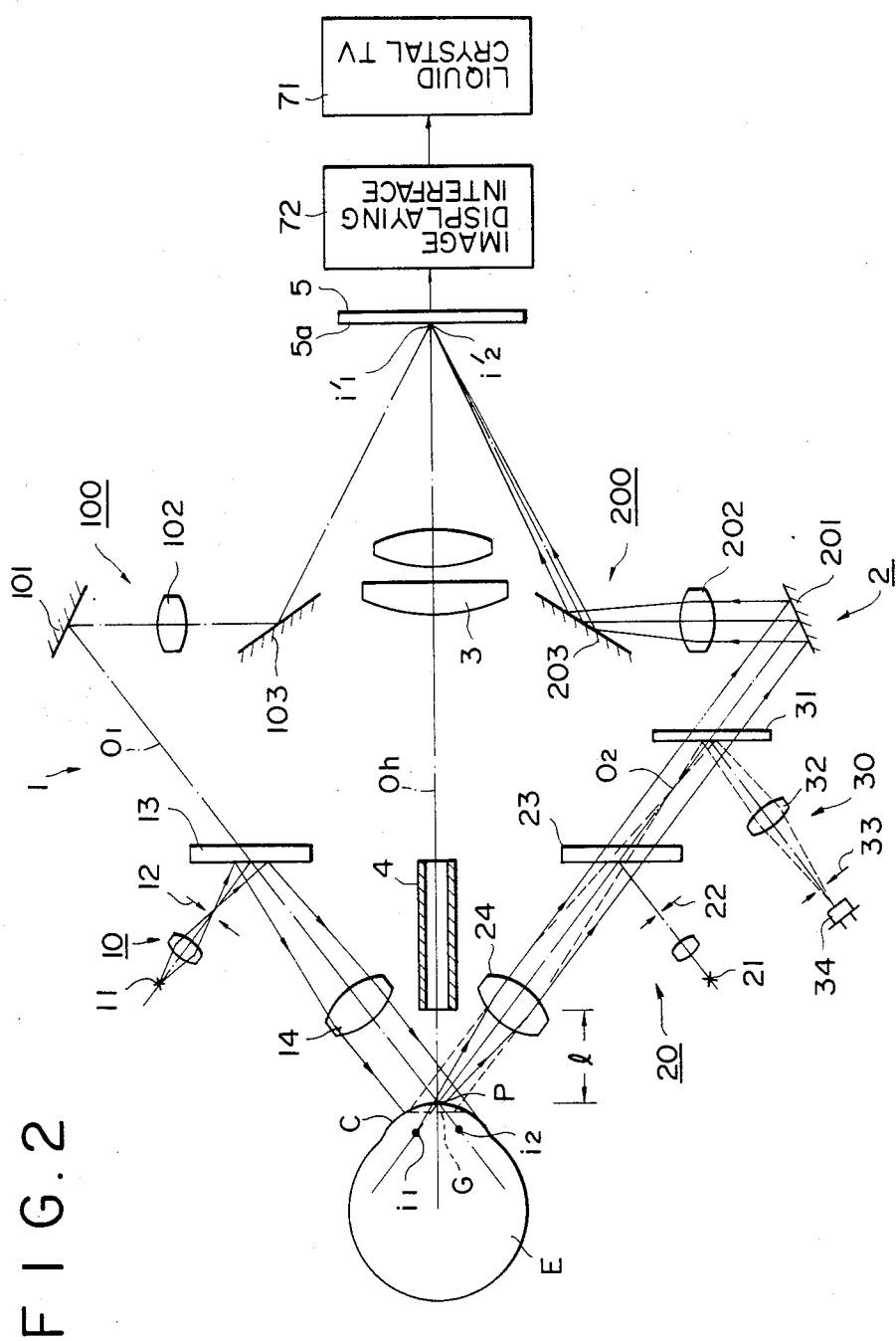
FIG. 2 is a schematic view showing an optical arrangement of an alignment detecting means which is employed in the embodiment.

FIG. 2 is a schematic view showing an optical arrangement for explaining an alignment detecting means A.

The alignment detecting means A includes a first optical means 1 and a second optical means 2. The first optical means 1 comprises a first target projecting optical means 10, and a first target image observing optical means 100 having an optical axis which is partly common to the axis of the the first target projecting optical means 10. The second optical means 2 comprises a second target projecting optical means 20 and a second target image observing optical means 200 which have the same optical constitution to the first optical means 1 with an axis $O_n$ served as a symmetry axis with respect to the first optical means 1.

A light emitted from a light source 11 of the first target projecting means 10 passes an aperture 12 as a target, is reflected by a half mirror 13, is converted into a parallel beam of light by an objective lens 14 having a focussing position at the aperture 12, and is then projected to the cornea C by the first target projecting optical means 10 as a target beam of light. The target beam of light is reflected by the cornea C and becomes a reflecting beam of light for forming a virtual image $i_1$ of the target 12 by the specular reflection of the cornea C. The reflecting beam of light which forms the virtual image $i_1$, passes a projecting lens 24 of the second optical means 2, passes a half mirror 23, and is then guided to a solid image pickup element 5 comprising, for example, an area CCD by mirrors 201 and 203 of the second target image observing optical means 200. In this embodiment, an imaging lens 202 is provided between the mirrors 201 and 203, and a target image $i_1'$ corresponding to the virtual image $i_1$ is formed on a photosensitive surface $5a$ of the area CCD 5 by the imaging lens 202. A signal of the target image $i_1'$ is input into a flat surface type displaying device 71 which comprises, for example, a liquid crystal TV, etc., as the displaying means 7 by an image displaying interface 72. As a result, the target image $i_1'$ is displayed on the flat surface type displaying device 71.

Similarly, a light emitted from a light source 21 which has passed an aperture 22 as a target of the second target image projecting optical means 20 of the second optical means 2, is reflected by the half mirror 23, is converted to a parallel beam of light by the projecting lens 24 having its focussing position at the aperture 22, and is then projected to the cornea C by the second target image projecting optical system 20 as the target beam of light. The target beam of light is reflected by the cornea C and becomes a reflecting beam of light for forming a virtual image $i_2$. The reflecting beam of light for forming the virtual image $i_2$ based on the specular reflection of the cornea C, passes through the projecting lens 14 of the first optical means 1, then passes through the half mirror 13, and is then guided to the solid image pickup element 5 by the mirrors 101 and 103 of the first target observing means 100. An imaging lens 102 is provided between the mirrors 101 and 103, and an target image $i_2'$ corresponding to the virtual image $i_2$ is formed on the photosensitive surface $5a$ of the area CCD 5 by the imaging lens 102.

When the intersecting points of the vertex P of cornea C, the respective optical axes $O_1$ and $O_2$ of the first and second optical means 1 and 2, and the axis $O_n$ of the nozzle 4 are overlapped at one point, the virtual images $i_1$ and $i_2$ are present on the focussing surface of the cornea C on the optical axes $O_1$ and $O_2$. At that time, the target images $i_1'$ and $i_2'$ are overlapped at one point on the photosensitive surface $5a$. When the target images $i_1'$ and $i_2'$ overlapped at one point on the photosensitive surface $5a$, the normal alignment is completed.

In FIG. 2, the alignment detecting means A has the objective lens 3 and is able to form an image of the anterior portion of the eye E on the photosensitive surface $5a$. As a result, the user of the device (observer) can observe the target images $i_1'$ and $i_2'$ and the image of the anterior portion by the flat surface type displaying device 71 simultaneously.

The second optical means 2 of the alignment detecting means A has an applanation detecting optical means 30 for detecting whether or not the cornea C of the eye E has been transfigured to applanation by the air pulse discharged from the nozzle 4. The applanation detecting optical means 30 comprises a half mirror 31, a relaying lens 32, an aperture 33, and a light receiving element 34. When the cornea E has been transfigured to applanation by the air pulse as shown by the broken lines, a target beam of light of the first optical means 1 is reflected by the applanation corneal surface G. The beam of light reflected by the applanation corneal surface G becomes a parallel beam of light and is guided to the light receiving element 43 by the relaying lens 32, etc. At that time, the optical amount of the target light detected by the light receiving element 34 becomes maximum.

Figure 3A:
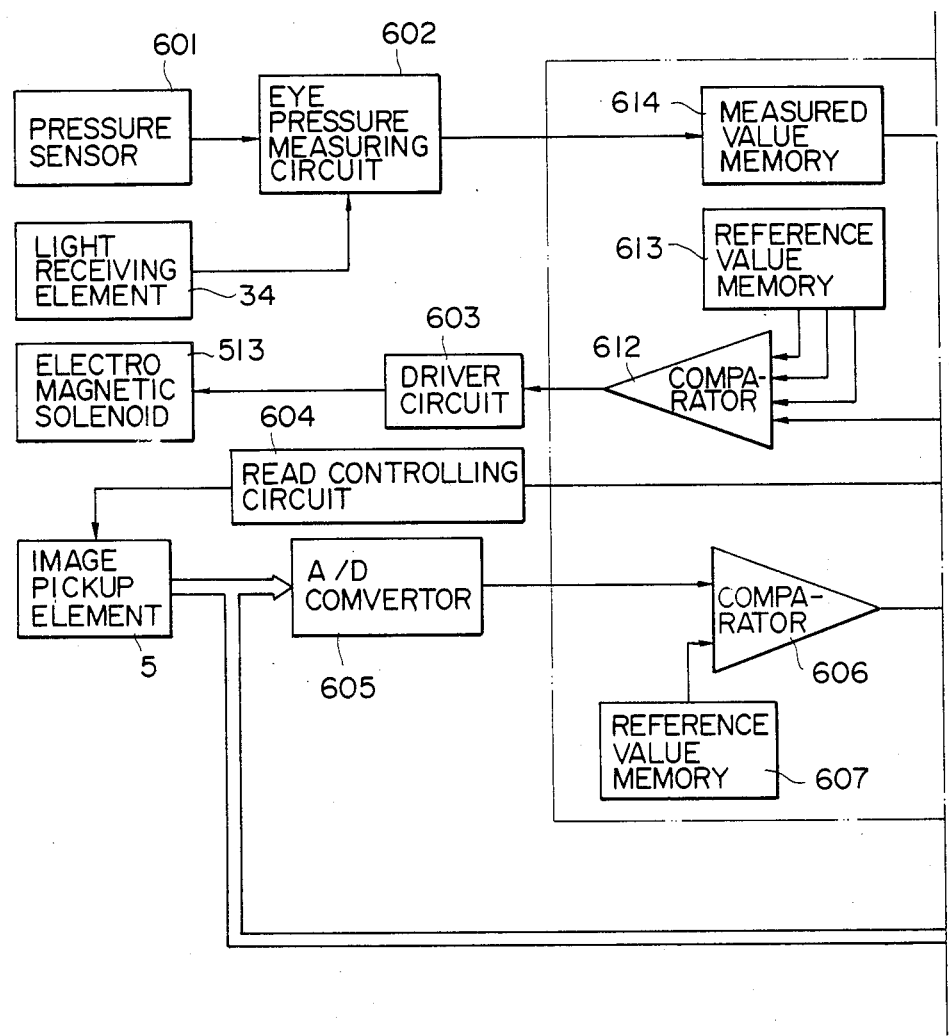
FIG. 3 is a block diagram showing electronic circuits.
Figure 3:
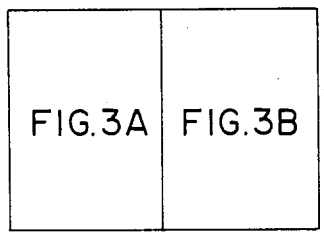
Figure 3B:
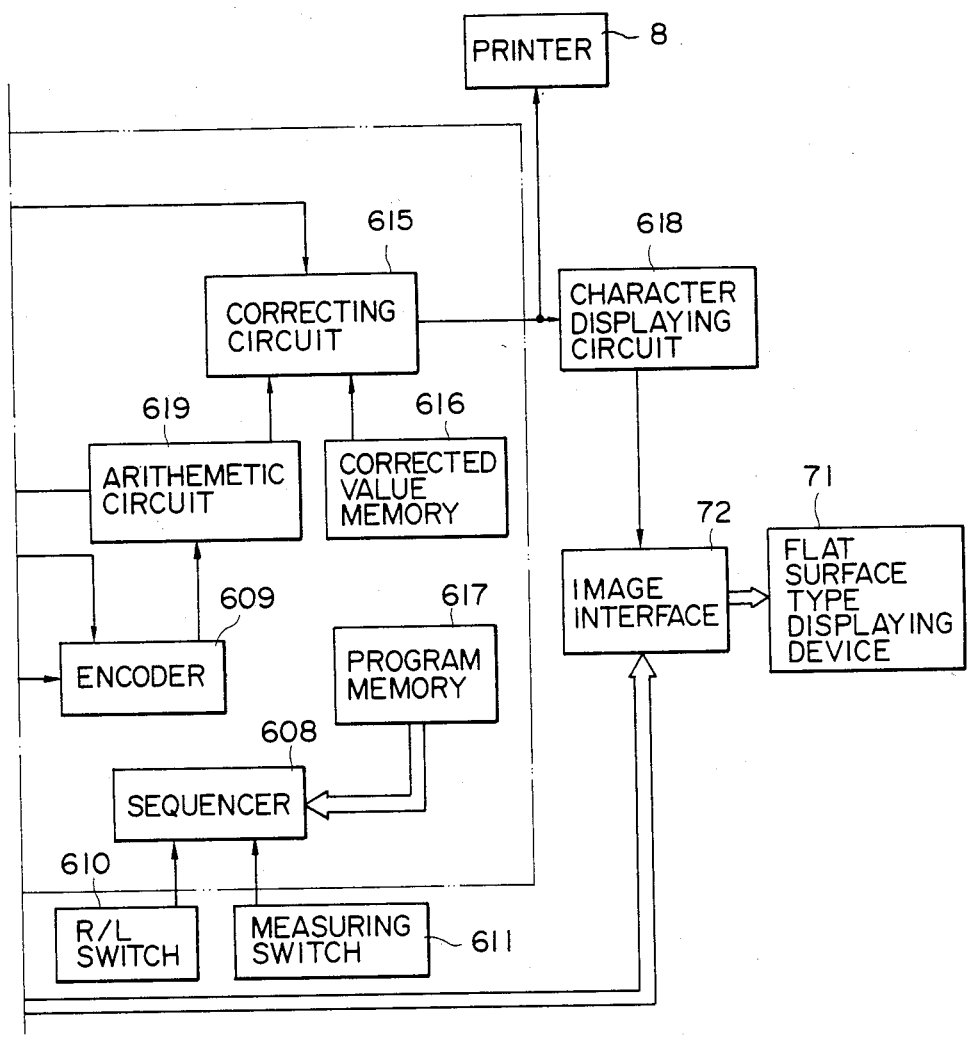

FIG. 3 is a schematic view showing the constitution of an electronic circuit 600. A pressure sensor 601 and the light receiving element 43 of the applanation detecting optical means 30 are connected with an eye pressure measuring circuit 602. The constitution of the eye pressure measuring circuit 602 is described in detail in U.S. patent application Ser. No. 743,417 which was filed by Susumu Takahashi and Fumio Ohtomo on June 11, 1985 and which has been assigned to the same assignee of the present application. The eye pressure measuring circuit 602 functions as a part of an eye pressure measuring means adapted to measure the eye pressure based on the pressure within an air chamber 52 which is obtained by the pressure sensor 601 during the air pulse is discharged. That is, the eye pressure measuring circuit 602 detects the light receiving amount of the light receiving element 34 every time when the air pulse has been increased by a unit pressure, and measures the eye pressure based on the pressure of the air pulse detected by the pressure sensor 601 when the light receiving amount has become the maximum or when the cornea C has been transfigured by a predetermined amount into applanation. This eye pressure measured value is stored in a measured value memory 614 as the actually measured eye pressure value $_iP$.

Figure 6:
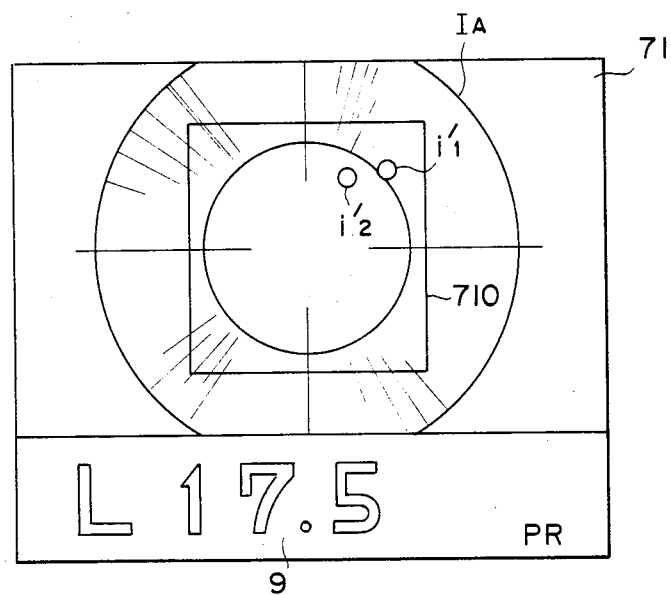
FIG. 6 is a schematic view showing one example of an image displayed on a displaying device.

The image pickup element 5 is scanned each of its image elements by a read controlling circuit 604 in turn. An image signal of the image pickup element 5 is input into a flat surface type displaying device 71 by an image interface 72. As a result, an anterior portion image $I_A$ of the eye E and the alignment target images $i_1'$ and $i_2'$ are simultaneously image displayed on the flat surface type displaying device 71 as shown in FIG. 6. An image signal of each image element of the image pickup element 5 is converted into a digital signal output by an A/D converter 605 and is input into a comparator 606. The comparator 606 has such a function as to compare an output from a reference value memory 607 with an output from the A/D converter 605 and select only image elements which have received the images $i_1'$ and $i_2'$ having a large light amount (brightness) with respect to the brightness of an image signal corresponding to the anterior portion image IA Then, the comparator 606 outputs a signal indicating a selection of the image elements which have received the target images $i_1'$ and $i_2'$ having a large light amount (brightness) to an encoder 609. The encoder 609 is already input with scanning image element addresses from the read controlling circuit 604. The encoder 609 seeks for the addresses which have been output from the comparator 606, i.e., the addresses $(X_{i1}, Y_{i1})(X_{i2}, Y_{i2})$ (hereinafter referred to as "target image receiving image element addresses") which have received the target images $i_1'$ and $i_2'$ according to the input of the signal from the comparator 606 and the input of the scanning image element addresses. An data of the target image receiving image element addresses $(X_{i1}, Y_{i1})(X_{i2}, Y_{i2})$ is input into a comparator 612 and a correcting circuit 615 by an arithmetic circuit 615. The arithmetic circuit 619 performs a calculation based on the following equations and seeks for an alignment position A $(X_i, Y_i,$ and $Z_i)$;

$$X_i = \frac{X_{i1} + X_{i2}}{2},$$

$$Y_i = \frac{Y_{i1} + Y_{i2}}{2}, Z_i = f(X_{i2} - X_{i1})$$

Figure 5:
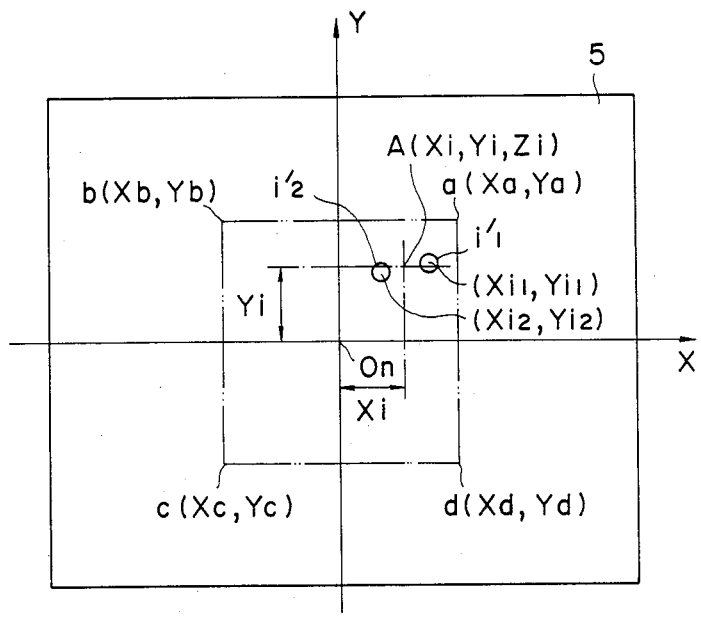
FIG. 5 is a schematic view showing an aligned position of a target image on an image pickup element.

The comparator 612 is input with an output from the reference value memory 613. As is shown in FIG. 5, the coordinate values $a(X_a, Y_a)$, $b(X_b, Y_b)$, $c(X_c, Y_c)$, and $d(X_d, Y_d)$ of the corner points of a rectangular area generally indicating the alignment completion area are stored in the reference value memory 613 in advance. The reference values $Z_1$ and $Z_m$ of a distance $\Delta Z = Z_1 - Z_m$ (see FIG. 7) generally indicating the alignment completion area of the tonometer in the Z axis direction (axis $O_n$ direction) are also stored in the reference value memory 613.

With the above-mentioned constitution, when the alignment position A $(X_i, Y_i,$ and $Z_i)$ which was obtained by the arithmetic circuit 619 based on the data of the target image receiving image element address $(X_{i1}, Y_{i1})(X_{i2}, Y_{i2})$ from the encoder 609, is within the rectangular area abcd, and $Z_i$ is determined to be $Z_1 < Z_i < Z_m$ by the comparator 612, the tonometer determines that the rough alignment has been completed. An output indicating the completion of the rough alignment is output from the comparator 612 to a driver circuit 603. Upon receipt of the output from the comparator 612, the driver circuit 603 excites the electromagnetic solenoid 513, causes the piston 511 to move upwards within the cylinder 510, compresses air within the cylinder 510, and discharges an air pulse from the nozzle 4. An actually measured eye pressure can be obtained by the aforementioned air pulse discharge. This measured eye pressure value $_iP(i=1, 2, 3 \ldots n)$ is stored in the measured value memory 614.

A correlation table as shown in table 1 is stored in a corrected value memory 616.

The correlation table shows the correlation relationship among the actually measured eye pressure value $_iP$, each component of X, Y and Z of the alignment position A $(X_i, Y_i, Z_i)$ at the time when the air pulse is discharged, and a corrected eye pressure value $_iP_{i,i,i}$ ($i = 1, 2, 3, \ldots 12$) which means as the normal eye pressure $P_o$ that will be obtained if the alignment is normally performed.

The correlation table is obtained based on experimental results in advance.

The correcting circuit 615 reads out the corrected eye pressure value $_iP_{i,i,i}$ as the normal eye pressure value $P_o$ from the correlation table memorized in the corrected value memory 616, in which the read out corrected eye pressure value $_iP_{i,i,i}$ is corresponding to the alignment position A $(X_i, Y_i, Z_i)$ calculated by the arithmetic circuit 619 and the measured eye pressure value $_iP$ memorized in the measured value memory 614.

For example, when the actually measured eye pressure value is $_1P$ and the alignment position is $A(X_1, Y_2, Z_2)$, the corrected eye pressure value or the normal eye pressure value is obtained $_1P_{122}$ from the corrected table.

The correcting circuit 615 outputs this corrected eye value $_1P_{i,i,i}$ to a character displaying circuit 618. The character displaying circuit 618 converts the output of the correcting circuit 615 into a value display which can be read by a natural person and displays the corrected eye pressure value 9 in character through the image displaying interface 72 as shown in FIG. 6.

Although the connecting state of the above-mentioned various circuitry elements is not illustrated in detail in FIG. 3, they are actuated according to a command of a sequencer 608 which is controlled by program stored in a program memory 617. Many circuitry elements including this sequencer 608 may comprise a microcomputer $\mu$COM. In this embodiment, the sequencer 608 is connected with a R/L switch 610 for inputting designating whether the eye E to be tested is a right eye or a left eye, and with a measuring switch 611 for commanding a start of measurement. The output of the correcting circuit 615 may be printed out by a printer 8 according to necessity.

FIG. 4 illustrates a flow chart for explaining the steps of measurement of the above-described noncontact type tonometer. First, a measurer or an operator designates whether the eye to be tested is a right eye or a left eye by the R/L switch 610 (Step S1). Upon receipt of the signal, the sequencer 608 determines whether the eye to be tested is a right eye or a left eye. The designation whether the right eye or the left eye is displayed on the flat surface type displaying device 71 by the character displaying circuit 618 and the image displaying interface circuit 72 as shown in FIG. 6. If the designation is, for example, the left eye, a character "L" is displayed (Steps S2 through S4).

Next, the measuring switch 611 is put on to perform an alignment manipulation of the tonometer with respect to the eye. That is, the measurer moves the tonometer forwards and backwards (Z direction), rightwards and leftwards (X direction), or upwards and downwards (Y direction) while watching the anterior portion image $I_A$ and the target images $i_1'$ and $i_2'$, so that both the target images $i_1'$ and $i_2'$ will be brought to be within a frame 710 of a reticle image corresponding to the rectangular area abcd (see FIG. 5) as the alignment completion area which is formed on the displaying screen by the character displaying circuit 618 and the distance between the target imaes $i_1'$ and $i_2'$ will become within a predetermined distance Z (Steps S5 through S7).

When the target images $i_1'$ and $i_2'$ have been brought to be within the frame 710 of the reticle image and the distance between the target images $i_1'$ and $i_2'$ has become within an interval corresponding to the predetermined distance Z, namely the rough alignment is performed, the comparator 612 excites the solenoid 513 using the driver circuit 603 to automatically discharge an air pulse as previously described (Step S8). And, the actually measured eye pressure value $_iP$ is corrected to $_iP_{iii}$ based on the actually measured eye pressure value of the eye pressure measuring circuit 602 and the alignment position A ($X_i$, $Y_i$, and $Z_i$) when the air pulse is discharged using the correcting circuit 615 and the corrected value memory 616, and the result is displayed on the flat surface type displaying device 71 as a corrected eye pressure value or normal eye pressure value $P_o$ or is printed out (Steps S9 through S13). For example, in the case the actually measured value $_iP$ is $_1P$, the value of the alignment position A is sought. If the alignment position A ($X_i$, $Y_i$, and $Z_i$) equals to A($X_1$, $Y_1$, and $Z_1$), the corrected eye pressure value $_1P_{111}$ corresponding thereto is obtained as the normal eye pressure value $P_o$ from the correlation table shown in Table 1 (see pages 18 and 19) which is stored in the corrected value memory 616.

Thereafter, the R/L switch is switched so as to display the character "R" indicating the right eye on the flat surface type displaying device 71, the tonometer is approached to the right eye, and the measuring switch 611 is put on. Thereafter, the same procedure to the left eye is followed to measure the eye pressure of the right eye. As described in the foregoing, according to the present invention, it is possible to provide a tonometer, in which even if the alignment between the nozzle of the fluid discharging means and the eye to be tested is somewhat rough, the actually measured eye pressure value obtained in the rough alignment state can be corrected based on the alignment error amount, and thereby a normal eye pressure value can be obtained.

TABLE 1

| Actually Measured Eye Pressure Value | Alignment Error | | | Corrected Eye Pressure Value |
|---|---|---|---|---|
| $_1P$ | | $Y_1$ | $Z_1$ | $_1P_{111}$ |
| | | | $Z_2$ | $_1P_{112}$ |
| | | | . | . |
| | | | . | . |
| | | | $Z_i$ | $_1P_{11i}$ |
| | | | . | . |
| | | | . | . |
| | | | $Z_n$ | $_1P_{11n}$ |
| | | $Y_2$ | $Z_1$ | $_1P_{121}$ |
| | | | $Z_2$ | $_1P_{122}$ |
| | | | . | . |
| | | | . | . |
| | | | $Z_i$ | $_1P_{12i}$ |
| | | | . | . |
| | | | . | . |
| | $X_1$ | | $Z_n$ | $_1P_{12n}$ |
| | | . | | |
| | | . | | |
| | | $Y_i$ | $Z_1$ | $_1P_{1i1}$ |
| | | | . | . |
| | | | . | . |
| | | | $Z_n$ | $_1P_{1in}$ |
| | | | . | . |
| | | | . | . |
| | | | $Z_1$ | $_1P_{1n1}$ |
| | | | . | . |
| | | | . | . |
| | | $Y_n$ | $Z_i$ | $_1P_{1ni}$ |
| | | | . | . |
| | | | . | . |
| | | | $Z_n$ | $_1P_{1nn}$ |
| | $X_2$ | $Y_1$ | $Z_1$ | $_1P_{211}$ |
| | | | . | . |
| | | | . | . |
| | | | $Z_i$ | $_1P_{21i}$ |
| | | | . | . |
| | | | . | . |
| | | | $Z_n$ | $_1P_{21n}$ |
| | | $Y_2$ | $Z_1$ | $_1P_{221}$ |
| | | | . | . |
| | | | . | . |
| | | $Y_n$ | $Z_n$ | $_1P_{2nn}$ |
| | $X_3$ | $Y_1$ | $Z_1$ | $_1P_{311}$ |
| | | . | | |
| | | . | | |

TABLE 1-continued

| Actually Measured Eye Pressure Value | Alignment Error | | | Corrected Eye Pressure Value |
|---|---|---|---|---|
| | $X_n$ | $Y_n$ | $Z_n$ | $_1P_{nnn}$ |
| $_2P$ | $X_1$ | $Y_1$ | $Z_1$ | $_2P_{111}$ |
| . | . | . | . | . |
| . | $X_n$ | $Y_n$ | $Z_n$ | $_2P_{nnn}$ |
| . | . | . | . | . |
| $_nP$ | $X_1$ | $Y_1$ | $Z_1$ | $_nP_{111}$ |
| . | . | . | . | . |
| | $X_n$ | $Y_n$ | $Z_n$ | $_nP_{nnn}$ |

What is claimed is:

1. A non-contact tonometer, comprising:
   fluid discharging means for discharging a pulse of fluid from a nozzle towards the cornea of an eye to be tested to transfigure the eye, said cornea having a vertex and said nozzle being movable into a predetermined alignment position relative to said vertex;
   means for measuring an intraocular pressure value of the eye to be tested in accordance with the pressure of said fluid pulse and the transfiguration of the eye;
   means for detecting an alignment error between said predetermined alignment position of said nozzle and the position of said nozzle relative said corneal vertex upon discharge of said fluid pulse; and
   means for correcting said measured intraocular pressure value in accordance with said detected alignment error to determine an actual intraocular pressure value.

2. The non-contact type tonometer according to claim 1, wherein said alignment error detecting means includes target projection means for projecting a plurality of target images toward the eye, and target image observing optical means for observing said target images formed on the eye by said target projecting means, said alignment error being defined at least in part in accordance with the positions of said target images relative one another.

3. The non-contact type tonometer according to claim 1, wherein the tonometer is disposed in a portable housing.

4. A non-contact tonometer, comprising:
   fluid discharging means for discharging a pulse of fluid from a nozzle towards the cornea of an eye to be tested to transfigure the eye, said cornea having a vertex and said nozzle being movable into a predetermined alignment position relative to said vertex;
   means for measuring an intraocular pressure value of the eye to be tested in accordance with the pressure of said fluid pulse and the transfiguration of the eye;
   means for detecting an alignment error between said predetermined alignment position of said nozzle and the position of said nozzle relative said corneal vertex upon discharge of said fluid pulse;
   means for correcting said measured intraocular pressure value in accordance with said detected alignment error to determine an actual intraocular pressure value;
   said correcting means including memory means for storing a functional relationship between discrete alignment error values and corresponding measured intraocular pressure values, said actual intraocular pressure value being calculated in accordance with said functional relationship.

5. The non-contact type tonometer according to claim 4, wherein said alignment error detecting means includes target projection means for projecting a plurality of target images toward the eye, and target image observing optical means for observing said target images formed on the eye by said target projecting means, said alignment error being defined at least in part in accordance with the positions of said target images relative one another.

6. The non-contact type tonometer according to claim 4, wherein the tonometer is disposed in a portable housing.

7. A non-contact tonometer, comprising:
   fluid discharging means for discharging a pulse of fluid from a nozzle towards the cornea of an eye to be tested to transfigure the eye, said cornea having a vertex and said nozzle being movable into a predetermined alignment position relative to said vertex;
   means for measuring an intraocular pressure value of the eye to be tested in accordance with the pressure of said fluid pulse and the transfiguration of the eye;
   means for detecting an alignment error between said predetermined alignment position of said nozzle and the position of said nozzle relative said corneal vertex upon discharge of said fluid pulse;
   means for correcting said measured intraocular pressure value in accordance with said detected alignment error to determine an actual intraocular pressure value;
   said correcting means including memory means for storing a functional relationship between discrete alignment error values and corresponding measured intraocular pressure values, said actual intraocular pressure value being calculated in accordance with said functional relationship; and
   said alignment error detecting means including target image projecting means for projecting a plurality of target images toward an anterior portion of the eye, and display means for displaying said anterior portion of the eye and said target images projected thereon.

8. The non-contact type tonometer of claim 7, wherein said display means includes a display surface for displaying said target images, means for detecting the positions of said target images on said display surface, and means for generating signals corresponding to said positions of said target images on said display surface.

9. The non-contact type tonometer of claim 8, including means, responsive to said signals generated by said generating means of said display means, for selectively actuating said fluid discharging means to discharge said fluid pulse.

* * * * *